(12) United States Patent
Takanori et al.

(10) Patent No.: US 6,325,760 B1
(45) Date of Patent: Dec. 4, 2001

(54) ROTATOR FOR ULTRASOUND PROBE

(75) Inventors: Satou Takanori, Funabashi; Tomita Norio, Kawaguchi; Nagai Hiroshi, Tokyo, all of (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/533,221

(22) Filed: Mar. 23, 2000

(30) Foreign Application Priority Data

Mar. 23, 1999 (JP) .................................................. 10-077931

(51) Int. Cl.[7] ...................................................... A61B 8/14
(52) U.S. Cl. ................................................................ 600/459
(58) Field of Search .................................. 600/407, 437, 600/443, 446, 447, 459, 463; 73/621–626

(56) References Cited

U.S. PATENT DOCUMENTS

| | | | |
|---|---|---|---|
| 4,494,548 | * 1/1985 | Buon et al. | 600/446 |
| 4,517,985 | * 5/1985 | Teslawski et al. | 600/446 |
| 5,152,294 | * 10/1992 | Mochizuki et al. | 600/459 |
| 5,465,724 | * 11/1995 | Sliwa, Jr. et al. | 600/459 |
| 5,779,639 | * 7/1998 | Yeung | 600/446 |

* cited by examiner

Primary Examiner—Marvin M. Lateef
Assistant Examiner—Ali M. Imam
(74) Attorney, Agent, or Firm—Hoffmann & Baron, LLP

(57) ABSTRACT

A rotator has an inner cylinder with a circular inner circumference surface, which is stored within a handy-type outer cylinder and rotatably driven by a motor, and a probe holder that is detachably inserted into the inner cylinder and which holds an ultrasound probe for providing two-dimensional image signals of body portions to be diagnosed by means of transmitting ultrasound beams in a stationary state. This probe holder has a cylindrical holder main unit arranged such that a cable extending from the rear end of the ultrasound probe is stored from the side of the holder, and a main unit fixing portion for fixing the holder main unit inserted into the inner cylinder to the inner cylinder, by pressing forwards. The holder main unit being pressed forward at the main unit fixing portion allows ultrasound probes having various outer circumference surfaces to be inserted such that the outer circumference thereof comes into contact at a position corresponding to the tapered position of the inner cylinder, and the tapered position of the holder main unit comes into contact with the outer circumference surface of the rear end portion thereof.

9 Claims, 4 Drawing Sheets

ROTATOR FOR ULTRASOUND PROBE

BACKGROUND OF THE INVENTION

1. Field of the Invention

The present invention relates to a rotator for ultrasound probes, for detachably storing and rotatably driving two-dimensional image ultrasound probes containing a transducer for transmitting ultrasound beams in a fan-shaped form by the sector scanning in order to obtain three-dimensional cross-sectional images of an area to be diagnosed in an organism.

2. Description of the Related Art

Japanese Unexamined Patent Publication No. 9-19431 discloses a rotation ultrasound probe wherein a cap provided to a tip surface of the transducer is placed against the area to be diagnosed, ultrasound jelly is introduced in the gap therebetween, and rotating a two-dimensional image transducer with a motor. Thus there is no need to directly place the transducer against the skin of the patient, thereby avoiding increasing the torque necessary for rotation, and also circumventing the problem of the measurement precision deteriorating due to the ease of central axis disorientation owing to relative action between the probe tip surface and the skin.

However, this rotational ultrasound probe has been configured exclusively for the rotational type, meaning that even in the event that the rotation is stopped for displaying a two-dimensional cross-section image of the area to be diagnosed on the ultrasound diagnostic equipment, extra components remain attached thereto. On the other hand, ultrasound diagnosis normally involves a process of first displaying a two-dimensional image and making a diagnosis therefrom, with three-dimensional images being displayed in this process as necessary. Also, in the event that a three-dimensional image apparatus is introduced anew, there is the need to also provide a rotational ultrasound probe such as described above anew, as well.

SUMMARY OF THE INVENTION

Accordingly, it is an object of the present invention to provide a detachable rotator for an ultrasound probe wherein various types of two-dimensional image ultrasound probes including already existing ones can be converted for three-dimensional image use with a simple operation.

The present invention is a rotator for an ultrasound probe, the rotator comprising: an inner cylinder with a circular inner circumference surface, which is stored within a handy-type outer cylinder and rotatably driven by a motor; and a probe holder which holds an ultrasound probe for providing two-dimensional image signals of body portions to be diagnosed by means of transmitting ultrasound beams in a stationary state, and detachably inserted into the inner cylinder; wherein the tip portion of the inner cylinder is formed as a tapered portion having an inner circumference surface which gradually decreases in inner diameter toward the rear side; and wherein the probe holder comprises: a cylindrical holder main unit which is formed as a tapered portion at the tip portion thereof having an inner circumference surface gradually increasing in inner diameter toward the rear side, and arranged such that a cable extending from the rear end of the ultrasound probe is stored from the side of the holder; and a main unit fixing portion for fixing the holder main unit inserted into the inner cylinder to the inner cylinder, by holding the ultrasound probe in the state of the tip portion outer circumference and the rear end portion outer circumference of the ultrasound probe being brought into contact with the tapered portion of the inner cylinder and the tapered portion of the holder main unit, respectively; with a gap formed between a cap which is attached to the tip portion of the outer cylinder and the tip plate of the ultrasound probe.

The ultrasound probe is inserted into the holder main unit from the front thereof in the state of the cable thereof being stored in the hollow interior of the cylindrical probe holder from the side. The outer circumference surface of the holder main unit corresponds with the inner diameter of the inner cylinder, so that the center axes in the state of being inserted into the rotator each match and are concentric. The holder main unit being pressed forward causes the outer circumference of the tip portion of the ultrasound probe, i.e., partway along the outer circumference surface thereof or the end thereof to come into contact with the tapered portion of the inner cylinder, and the tapered portion of the holder main unit comes into contact with the outer circumference of the rear end portion. Accordingly, as long as the outer circumference of the front and rear end portions have a circular portion at least partially over a range of 180° or more, a concentric state is achieved with the rotator by the contact at the tapered portion. The holder main unit which holds the ultrasound probe with the state of contact with the front and rear tapered potions is fixed to the inner cylinder by the main unit fixing portion, and rotates together with the inner cylinder. Ultrasound jelly is filled in the gap between the tip surface of the ultrasound probe and the cap.

Accordingly, two-dimensional image ultrasound probes of various shapes can be detachably mounted to the rotator and converted for use as three-dimensional image probes. The ultrasound probe is hold in a concentric state with the rotator even in the event that the length thereof or the form at the front and rear ends differ, by means of concentric insertion of the holder main unit into the rotator, and by the circular outer circumference at the front and rear of the ultrasound probe coming into contact with the tapered portions in the inner cylinder and the holder main unit. Operation of the holder main unit is a simple insertion and removal process.

The main unit fixing portion may be slidably inserted into the holder main unit from the rear so as to follow the center axis, in an arrangement wherein the rotator further comprises: a cylindrical holder base portion into which the cable is stored from the side; and lock buttons which are slidably guided along guide grooves formed to the holder main unit in the radial direction thereof as to the center axis, so as to come into contact with the inner circumference surface of the inner cylinder at the front-most outwards position; wherein a slave portion, driven outwards in the state of being in contact with the driving portion in accordance with the progression of the driving portion formed to the tip portion of the holder base portion, is formed the base portion of the lock buttons; whereby fixing of the holder main unit to the inner cylinder can be easily performed by an inserting and removing operation of the holder base portion, which drives the lock buttons in a friction-retained state, and also the configuration is simple.

The outer circumference surface of the tip portion of the holder base portion may be formed as a tapered portion gradually inclined backwards toward the outside, so as to form a driving surface as a driving portion, and also have an outer diameter corresponding to the inner diameter of the holder main unit at the rear area of the tapered portion at the holder base portion, with a sliding portion formed retained at a retaining flange at the rear end of the holder main unit; this arrangement involving lock buttons being erected at a plurality of positions of outer circumference surface of an arc spring, and the inner circumference surface of the arc spring being formed as an inclined plate gradually inclining outwards toward the rear direction so as to form a slave surface as a slave portion; wherein the lock buttons are easily configured of a single ring-shaped part exhibiting spring force, and a driving surface is easily formed to the holder base portion by tapering. Removal from the holder main unit is restricted, and the locking operation can be easily performed with sliding of high positional precision.

An opening for storing the cable from the side to the hollow interior may be formed to the holder main unit and the holder base portion, so the configuration can be easily achieved by simply notching out the probe holder, taking advantage of the closed form of the rotator, also facilitating ease in the insertion operation of the cable.

Slide pins may be erected from one of either the tip or front surface of the holder base portion or the rear surface of the holder main unit, and guide holes be formed to the other for guiding the slide pins, with an elastic member being mounted between the tip surface and the rear surface so as to press to mutually distance the tip surface and the rear surface; with a sliding portion having an outer diameter corresponding to the inner diameter of the inner cylinder being formed at an area further rearwards than the portion of the holder base portion which is inserted into the holder main unit; whereby the probe holder is stored concentrically to the rotator with an even higher level of positional precision. The relative rotation between the holder base portion and the holder main unit is prevented, and the cable storing configuration is also simplified. The holder base portion is positioned at a predetermined position in the normal state by the spring force, thus facilitating ease of operation.

DETAILED DESCRIPTION OF THE PREFERRED EMBODIMENTS

Figure 1:
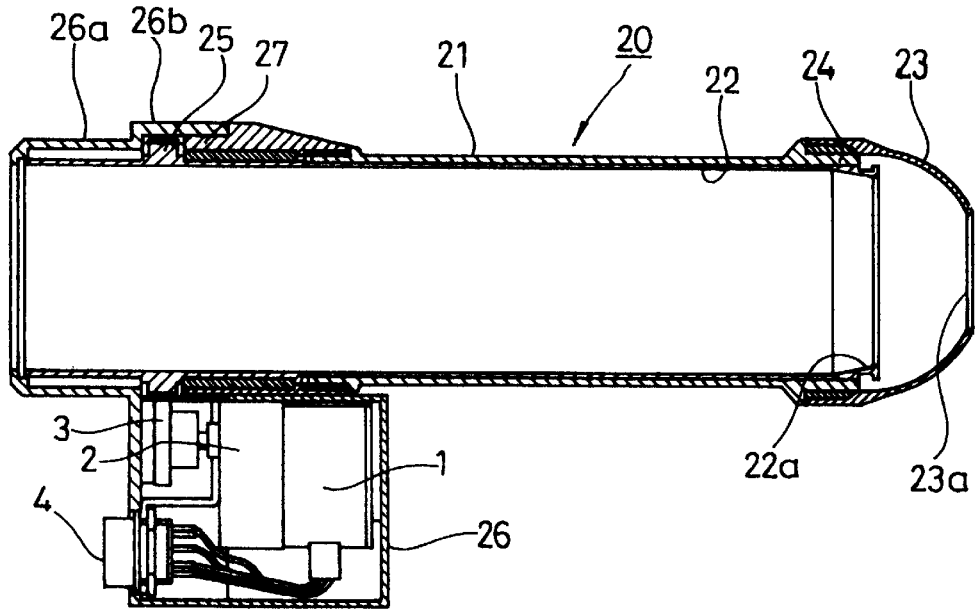
FIG. 1 is a cross-sectional diagram of a rotator according to an embodiment of the present invention.
Figure 1:
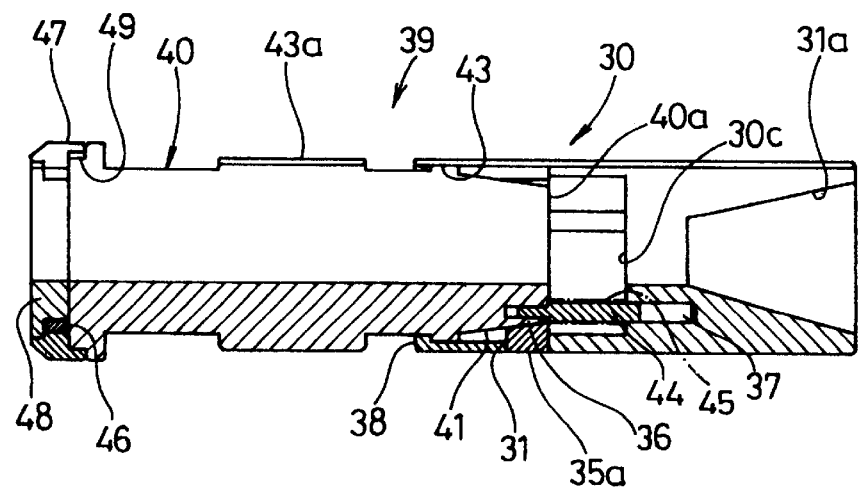

An example of a rotator for ultrasound probes according to an embodiment of the present invention will be described with reference to FIGS. 1 through 5. In FIG. 3, reference numeral 10 denotes an example of an ultrasound probe, having at the tip portion thereof a transducer which scans ultrasound transmitting beams in a fan-shaped manner so as to supply two-dimensional image signals of a portion of a subject to be diagnosed. Such ultrasound probes are not restricted in form to that shown in the drawing; rather, various types exist. However, a characteristic commonly shared among handy-type ultrasound probes is a shape with a circular circumference, having a tip portion 11 to which a raised portion 11a for latching one's finger onto is formed, and comprising a rear end portion 13 which gradually grows smaller toward the outer diameter of the cable 12 extending therefrom. In this case, the tip portion 11 gradually diminishes in diameter toward the transducer surface of a diameter corresponding to the spacing between ribs to deal with the heart and other tissue.

FIG. 1 illustrates a rotator 20, wherein an inner cylinder 22 is guided along the inner circumference surface of the outer cylinder 21 of a handy-type ultrasound probe so as to be rotatably stored therein, with a probe holder 39 also being provided thereto. Fit to the rear end portion of the outer cylinder 21 is the cylindrical holder 26a of a motor storing case 26 wherein are contained a stepper motor 1, a gear 3 which is linked to the rotational shaft thereof by a speed reducer 2, a connector 4 for input of motor driving signals, and so forth, with a raised step portion 26b thereof further fitting with an arc-shaped fitting base 27.

A gear 25 is formed to the perimeter of the inner cylinder 22 over a range of 360° (necessary at least about 180°), which protrudes from a notch formed in the outer cylinder 21 and meshes with the gear 3. The outer cylinder 21 has formed on the tip portion thereof a ring-shaped fitting base 24, and a half-spherical cap 23 which is formed of an ultrasound-transmitting material detachably fits thereto. An opening 23a, which faces the probe tip surface 1b corresponding to the tip surface form of the transducer of the ultrasound probe 10 is formed to the center portion of this cap.

Further, the tip portion of the inner cylinder 22 is formed as a tapered portion 22a which has a inner circumference surface which gradually increases in inner diameter toward the rear side, such that the tip portion 11 of the ultrasound probe 10 inserted from the rear comes into contact therewith. The range of change in the inner diameter of this tapered portion is set such that the end of the tip portion outer circumference of common two-dimensional image probes with differing outer diameters and/or longitudinal lengths, or the outer circumference surface along the side thereof, will come into contact therewith. The position of the opening 22a in the longitudinal direction is set such that a gap is left for a probe tip surface 11b which is expected to be mounted.

Figure 2:
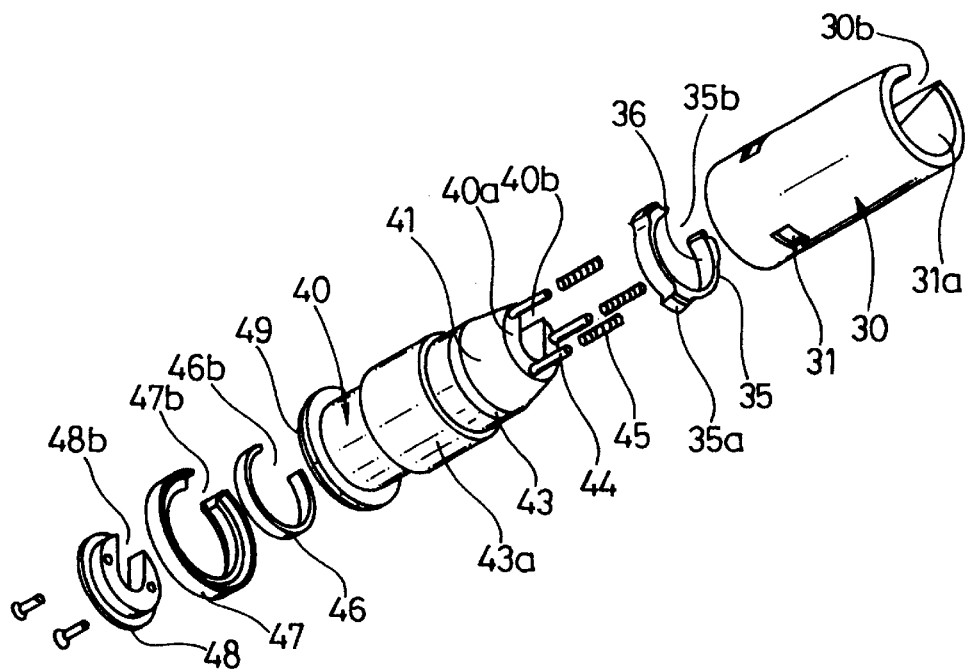
FIG. 2 is a perspective view of the probe holder portion of the rotator.
Figure 3:
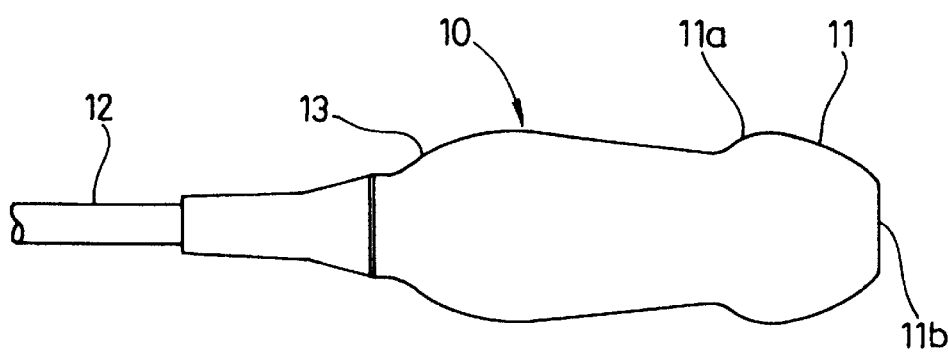
FIG. 3 is a perspective view of a two-dimensional image ultrasound probe.

As shown in FIGS. 1 and 2, the probe holder 39 comprises a cylindrical holder main unit 30 which is formed as a tapered portion 31a which has an inner circumference surface such that the tip portion gradually decreases in diameter toward the rear, so that the rear end portion 13 of the ultrasound probe 10 comes into contact therewith and has an outer diameter corresponding to the inner diameter of the inner cylinder 22, and a main unit fixing portion formed of a cylindrical holder base portion 40 and a lock button 35a. The holder base portion 40 has the tip portion outer circumference surface thereof formed as a tapered driving surface 41 gradually inclined outwards toward the rear, so as to be slidably inserted from the rear in the longitudinal direction following the inner circumference surface of the holder main unit, and also so as to form a driving portion. Three lock buttons 35a are erected on the arc-shaped spring 35.

These lock buttons are slidably guided through three guide grooves 31 formed at three positions on the circumference of the holder main unit 30 at a certain longitudinal position in a radial direction from the central axis thereof. Also, the inner circumference surface of this arc-shaped spring, i.e., the base portion of the lock buttons 35a, is tapered so as to serve as a slave surface 36 gradually inclined outwards, toward the rear. Thus, in the process of pressing the probe holder 39 into the inner cylinder 22, the base portion of the lock buttons 35a serves as a slave portion which is widened and driven by the driving plane 41 progressing and coming into contact at the front-most position in the radial direction.

Three slide pins 44 are erected from the tip surface 40a of the holder base portion 40 with spacing in the circumference direction, and guide holes 37 for guiding these slide pins are formed from the rear end surface 30c of the holder main unit 30 in a corresponding manner, with a coil spring 45 being mounted to each slide pin 44 so as to provide pressing force to distance the tip surface 40a and the rear end surface 30c. Also, a sliding portion 43 of the holder main unit is formed further behind the driving surface 41 of the holder base portion 40, in a bulging ring form which has an outer diameter corresponding with the inner diameter of the rear end portion of the holder main unit 30, so as to be retained by the retaining flange 38 at the rear end of the holder main unit 30. Accordingly, the holder base portion 40 can smoothly slide by being guided by the slide pins 44 with the guide holes 37, relative rotation is also restricted, and the holder main unit 30 does not fall away form the holder base portion 40, due to the retaining flange 38.

Even further behind the sliding portion 43 is formed an inner cylinder sliding portion 43a which has an outer diameter corresponding to the inner diameter of the inner cylinder 22. Accordingly, the sliding portion 43a is inserted in a state of being in contact with the inner circumference surface of the inner cylinder 22, as well as the outer circumference surface of the holder main unit 30, so mating of the center axis is secured for each, with high positional precision.

The holder main unit 30 and the holder base unit 40 are cylindrical forms with hollow interiors, the relative rotation thereof having been restricted, and openings 30b and 40b which are sufficiently narrower than 180° are formed along the central axes as entrances for storing the cable 12 which is extended from the rear end of the ultrasound probe 10. The arc-shaped spring 35 naturally has an opening 35b. Also, shuttering 47 for the cable is rotatably mounted to the circular buide surface 49 formed at the rear end portion of the holder base portion 40 by means of a ring-shaped pressing member 48 being bolted in place, rotatably operable with friction provided a sponge 46. In the same manner, openings 46b, 47b, and 48b are opened in the sponge 46, shuttering 47, and ring-shaped pressing member 48.

Figure 4:
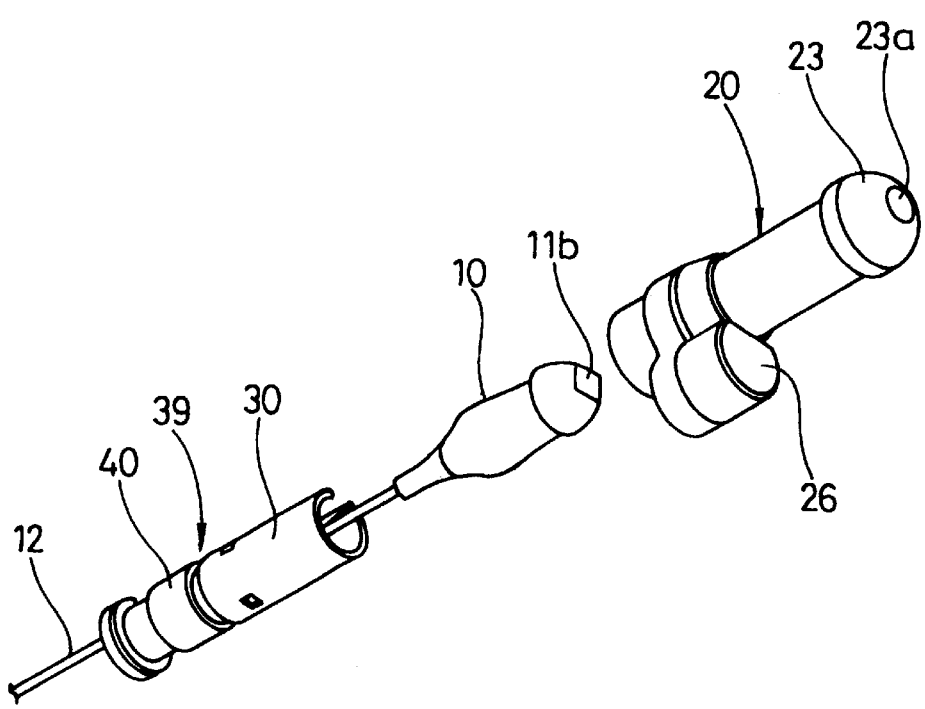
FIG. 4 is a perspective view for describing the attaching/detaching operation of the rotator.
Figure 5:
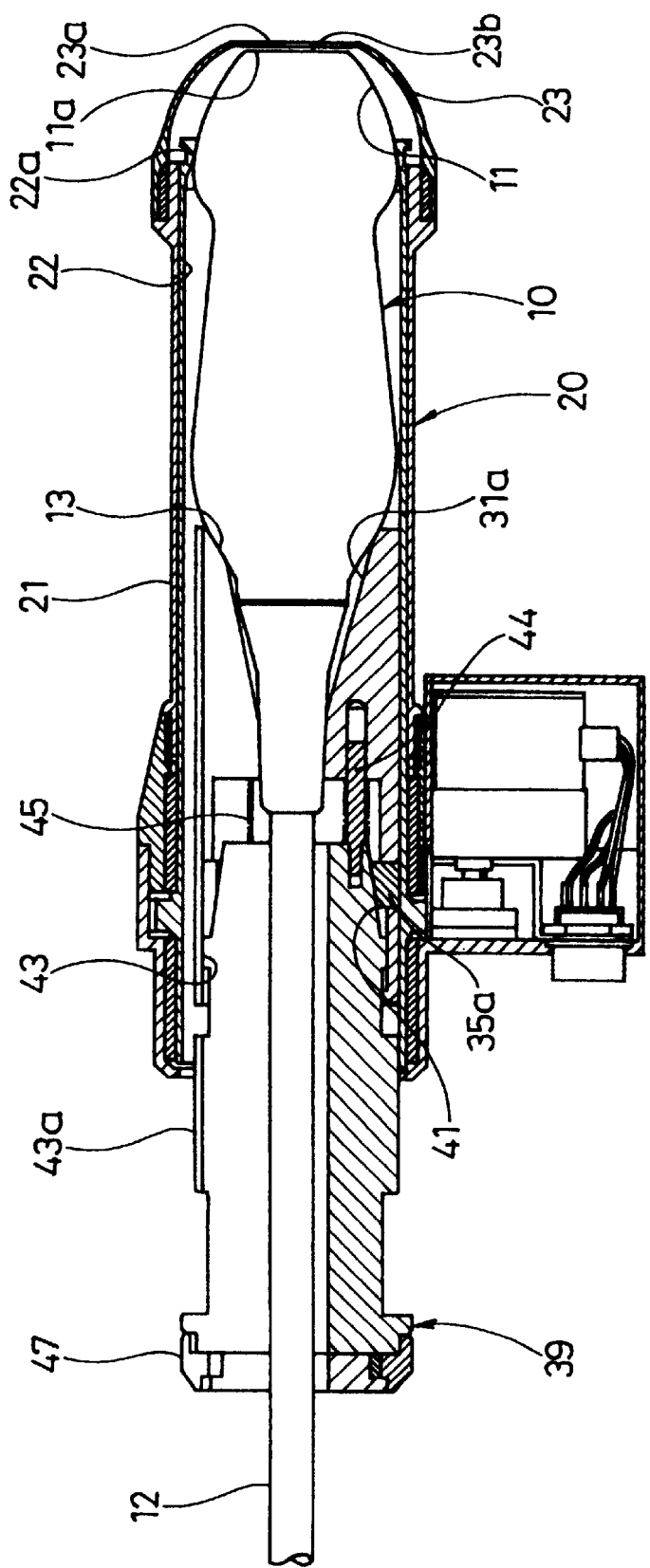
FIG. 5 is a cross-sectional diagram of state wherein the ultrasound probe is mounted to the rotator.

The operation method and operation of the rotator 20 thus configured is as follows. In the event that a three-dimensional image is necessary for diagnosis, a portion partway through the cable 12 connected to the ultrasound diagnostic equipment at the end portion thereof is inserted from the openings 30b, 35b, 40b, 46b, 47b, and 48b, in the probe holder 39, as shown in FIG. 4, and the shuttering 47 is closed with a rotating operation so as to hold with the cylindrical probe holder 39. Next, the ultrasound probe 10 is inserted into the holder main unit 30 and inserted into the inner cylinder 22 of the rotator 20, following which pressing the holder base portion 40 forwards brings the tip portion 11 thereof into contact with the tapered portion 22a of the inner diameter position corresponding with the outer diameter thereof, and the rear end portion 13 comes into contact with the tapered portion 13a of the inner diameter position corresponding to the outer diameter thereof. Further causing process against the force of the coil springs 45 causes the driving surface 41 to drive the slave surface 36 thereof against the elastic force of the arc-shaped spring 35, the tip surface of the lock button 35a come into contact with the inner circumference surface of the inner cylinder 22, thereby restricting forward progression.

Thus, the state of contact of the ultrasound probe 10 against to the forward and rearward tapered portions 22a and 31a is locked with the friction-engagement between the driving surface 41 and the slave surface 36, even in the event that the pressure of the holder base portion 40 is disengaged. The insertion operation of the holder base portion 40 is performed to the extent that locking can be performed in a sure manner against the reaction force of the arc-shaped spring 35 and the coil springs 45. Accordingly, the probe holder 39 is inserted in the rotator 20 in a concentric manner, and the circular outer circumferences of the front and rear portions 11 and 13 of the ultrasound probe 10 come into contact with the front and rear tapered portions 22a and 31a, thereby storing the ultrasound probe 10 in the rotator 20 so that the central axes of each are concentric (See FIG. 5).

With the present invention, the ultrasound probe is not restricted to such as shown in the drawings; rather, any ultrasound probes are similarly stored in a concentric manner even with different forms, as long as these are in a range wherein the circular outer circumferences of the front and rear end portions come into contact with the front and rear tapered portions 22a and 31a. Even in the event that the ultrasound probe does not have a tapered form at the rear end portion but is a simple cylindrical form, the end of the outer circumference surface comes into contact, and accordingly the ultrasound probe is similarly stored in a concentric manner.

Ultrasound jelly which has ultrasound transmitting properties exhibiting acoustic coupling action is filled in the gap 23b through the opening 23a and decay of the ultrasound beam is prevented, in which state the edge of the opening 23a is placed against the portion to be diagnosed and the rotator 20 is operated, whereby the inner cylinder 22 automatically rotates forwards and backwards within a 180° range, the rotational force is propagated by the junction of the lock buttons 35a and tip portion 11 to the inner cylinder 22a, so that three-dimensional scanning is performed by the rotation of the fan-shaped ultrasound beam.

In the event that the holder base portion 40 is extracted from the rotator 20 in order to use the ultrasound probe 10 in a normal state, the lock buttons 35a retreat by the elastic returning force of the arc-shaped spring 35 and are unlocked, so removal is easy. Further, the holder base portion 40 is removed in a sure manner from the holder main unit 30 by the returning force of the coil springs 45, and the sliding portion 43 returns to the position of being retained by the retaining flange 38, so the lock buttons 35a are restrained within the guide grooves 31 without protruding from the outer circumference surface of the holder main unit 30.

Incidentally, in the case that the rotator 20 hasn't opening 23a provided to the cap 23, as a separate embodiment, a three-dimensional beam can be irradiated to the area to be diagnosed by forming an ultrasound jelly insertion opening at one side thereof and filling this with ultrasound jelly so that there is no gap at the tip surface 11a of the ultrasound probe 10, with only minute decay according to the selection of the material of the cap 23. Further, in the event that a somewhat more complex arrangement can be tolerated, a plurality of lock buttons having slave surfaces formed on the base portions thereof may be independently formed in the same circumference direction, with coil springs or the like mounted around each at the inner side of the holder main unit 30, so as to provide pressing force inwards.

Also, an arrangement may be made wherein screw threads are formed at the rear side of the driving surface of the holder base portion, so as to drive forward by screwing instead of sliding. In this case, an arrangement can be conceived wherein the slid pins with coil springs are done away with between the tip surface thereof and the rear end surface of the holder main unit; with sponge rubber introduce therebewteen instead. Also, an arrangement may be made wherein screw threads are formed on the circumference surface of the main unit fixing member itself serving as a housing having an opening for the cable 12, this being made to mesh with screw threads formed on the inner circumference surface of the rear end of the inner cylinder, thereby pressing the holder main unit in directly. Further, an arrangement may be conceived wherein, instead of the cable inserting opening which vertically traverses the probe holder, the rearwards portion where there is no insertion of the holder base portion is divided vertically, with one serving as an opening and closing lid from the side, or other such arrangements may be conceived.

What is claimed is:

1. A rotator for an ultrasound probe, said rotator comprising:

a handy-type outer cylinder to which a motor is provided;

an inner cylinder which is stored inside said outer cylinder and is rotatably driven by said motor, having a circular form for the inner circumference surface thereof; and a probe holder which holds an ultrasound probe for providing two-dimensional image signals of body portions to be diagnosed by means of transmitting ultrasound beams in a stationary state, and detachably inserted into said inner cylinder;

wherein the tip portion of said inner cylinder is formed as a tapered portion having an inner circumference surface which gradually increases in inner diameter toward the rear side:

and wherein said probe holder comprises; a cylindrical holder main unit which is formed as a tapered portion at the tip portion thereof having an inner circumference surface, has an outer circumference surface of an outer diameter corresponding to the inner diameter of said inner cylinder, and arranged such that a cable extending from the rear end of said ultrasound probe is stored from the side of said holder, said inner circumference surface gradually decreasing in inner diameter toward the rear side; and a main unit fixing portion for fixing said holder main unit inserted into said inner cylinder to said inner cylinder, by holding said ultrasound probe in the state of the tip portion outer circumference and the rear end portion outer circumference of said ultrasound probe being brought into contact with said tapered portion of said inner cylinder and said tapered portion of said holder main unit, respectively;

and wherein a cap is attached to the tip portion of said outer cylinder, with a gap formed between the tip plate of said ultrasound probe in contact with said tapered portion of said inner cylinder and said cap.

2. A rotator for an ultrasound probe according to claim 1, wherein said main unit fixing portion comprising:

a cylindrical holder base portion which is slidably inserted into said holder main unit from the rear so as to follow the center axis and is stored with said cable from the side; and lock buttons which are slidably guided along guide grooves formed to said holder main unit in the radial direction thereof as to the center axis, so as to come into contact with the inner circumference surface of said inner cylinder at the front-most outwards position;

and wherein a slave portion, driven outwards in the state of being in contact with said driving portion in accordance with the progression of said driving portion formed to the tip portion of said holder base portion, is formed the base portion of said lock buttons.

3. A rotator for an ultrasound probe according to claim 2, wherein the outer circumference surface of said tip portion of said holder base portion is formed as a tapered portion gradually inclined backwards toward the outside, so as to form a driving surface as a driving portion, has an outer diameter corresponding to the inner diameter of said holder main unit at the rear area of said tapered portion at said holder base portion, with a sliding portion formed which is retained at a retaining flange at the rear end of said holder main unit;

wherein lock buttons are erected at a plurality of positions of outer circumference surface of an arc-shaped spring, and the inner circumference surface of said arc-shaped spring is formed as an inclined plate gradually inclining outwards toward the rear direction so as to form a slave surface as a slave portion.

4. A rotator for an ultrasound probe according to claim 2, wherein openings for storing said cable from the side to the hollow interior are formed to said holder main unit and said holder base portion.

5. A rotator for an ultrasound probe according to claim 2, wherein slide pins are erected from one of either the tip surface of said holder base portion or the rear surface of said holder main unit, and guide holes are formed to the other for guiding said slide pins, with an elastic member being mounted between said tip surface and said rear surface so as to press to mutually distance said tip surface and said rear surface;

and wherein a sliding portion having an outer diameter corresponding to the inner diameter of said inner cylinder is formed at an area further rearwards than the portion of said holder base portion which is inserted into said holder main unit.

6. A rotator for an ultrasound probe according to claim 1, wherein an opening is formed at the cap area facing a transducer surface provided to the tip portion of said ultrasound probe.

7. A rotator for an ultrasound probe according to claim 1, wherein said motor rotates said inner cylinder within a range of 180° forwards and backwards, by means of a gear being formed over a range of at least 180° on the outer circumference of said inner cylinder so as to mesh with a gear driven by said motor via a notch formed on the outer cylinder.

8. A rotator for an ultrasound probe according to claim 1, wherein said main unit fixing portion comprises:

a cylindrical holder base portion which is provided with screw threads on the outer circumference surface thereof engaging screw threads formed on the inner circumference surface of said holder main unit, and is arranged such that said cable is stored thereto from the side; and lock buttons which are slidably guided along guide grooves formed to said holder main unit in the radial direction thereof as to the center axis, so as to come into contact with the inner circumference surface of said inner cylinder at the front-most outwards position;

and wherein a slave portion, driven outwards in the state of being in contact with said driving portion in accordance with the progression of said driving portion formed to the tip portion of said holder base portion, is formed the base portion of said lock buttons.

9. A rotator for an ultrasound probe according to claim 1, wherein said main unit fixing portion is a cylindrical member with an opening for storing said cable from the side to the hollow interior formed thereto, and is provided with screw threads on the outer circumference surface thereof which engage screw threads formed on the inner circumference surface of the end portion of said inner cylinder.

* * * * *

UNITED STATES PATENT AND TRADEMARK OFFICE
CERTIFICATE OF CORRECTION

PATENT NO. : 6,325,760 B1
DATED : December 4, 2001
INVENTOR(S) : Satou et al.

It is certified that error appears in the above-identified patent and that said Letters Patent is hereby corrected as shown below:

<u>Title page,</u>
Item [12], Patent Name now reads "Takanori et al." should read -- Satou et al. --
Item [75], Inventors now reads "Satou Takanori, Funabashi; Tomita Norio, Kawaguchi; Nagai Hiroshi, Tokyo, all of (JP)" should read -- Takanori Satou, Funabashi; Norio Tomita, Kauaguchi; Hiroshi Nagai, Tokyo, all of (JP) --

Signed and Sealed this

Third Day of September, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.    : 6,325,760 B1
DATED         : December 4, 2001
INVENTOR(S)   : Satou et al.

It is certified that error appears in the above-identified patent and that said Letters Patent is hereby corrected as shown below:

<u>Title page,</u>
Item [12], now reads "Takanori et al." should read -- Satou et al. --
Item [75], Inventors now reads "Satou Takanori, Funabashi; Tomita Norio, Kawaguchi; Nagai Hiroshi, Tokyo, all of (JP)" should read -- Takanori Satou, Funabashi; Norio Tomita, Kawaguchi; Hiroshi Nagai, Tokyo, all of (JP) --

Signed and Sealed this

Ninth Day of September, 2003

JAMES E. ROGAN
*Director of the United States Patent and Trademark Office*